United States Patent [19]

Desmond et al.

[11] Patent Number: 5,585,504

[45] Date of Patent: Dec. 17, 1996

[54] PROCESS OF MAKING COX-2 INHIBITORS HAVING A LACTONE BRIDGE

[75] Inventors: Richard Desmond, Bridgewater; Ulf Dolling, Westfield, both of N.J.; Ben Marcune, Bayside, N.Y.; Richard Tillyer, Scotch Plains; David Tschaen, Holmdel both of N.J.

[73] Assignee: Merck & Co., Inc., Rahway, N.J.

[21] Appl. No.: 307,972

[22] Filed: Sep. 16, 1994

[51] Int. Cl.$^6$ ................................................. C07D 307/58
[52] U.S. Cl. ................................................................. 549/323
[58] Field of Search ............................................ 549/323

[56] References Cited

FOREIGN PATENT DOCUMENTS

| | | |
|---|---|---|
| 0623606 | 11/1994 | European Pat. Off. . |
| WO94/15932 | 7/1994 | WIPO . |

OTHER PUBLICATIONS

Campbell, et al., J. Chem. Soc., Perkin Trans. 1, No. 8, pp. 1567–1576 (1985).

Ford, et al., J. Org. Chem., vol. 32, No. 1, pp. 173–177 (1967) Eastman Kodak Co., Res. Labs Rochester, NY.

Dikshit, et al., Indian Journal of Chemistry, vol. 29b, pp. 954–960 (1990).

*Primary Examiner*—Amelia Owens
*Attorney, Agent, or Firm*—Curtis C. Panzer; David L. Rose

[57] ABSTRACT

The invention encompasses a process for making compounds of Formula I useful in the treatment of cyclooxygenase-2 mediated diseases.

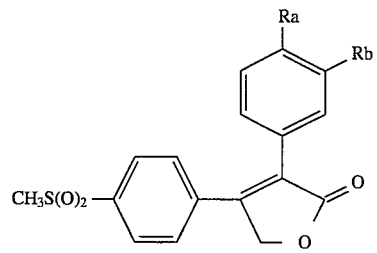

14 Claims, No Drawings

PROCESS OF MAKING COX-2 INHIBITORS HAVING A LACTONE BRIDGE

BACKGROUND OF THE INVENTION

This invention concerns a process for making certain antiinflammatory compounds. In particular, the application concerns a process for making compounds of formula I as disclosed hereinunder, which compounds are potent cyclooxygenase-2 inhibitors.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

WO 94/15932 published Jul. 21, 1994 discloses a multistep method of making bi-aryl furans via bi-aryl lactones, which method utilizes a keto-ester internal cyclization to the lactone. We have found that a significant amount of undesired by-products are produced by use of the disclosed process scheme, due to the external cyclization reactions which compete with the desired internal cyclization. While these by-products can be removed by suitable separation and purification techniques, we have sought to identify alternative processes to obviate the difficulties.

SUMMARY OF THE INVENTION

The invention encompasses a process for making compounds of Formula I useful in the treatment of inflammation and other cyclooxygenase-2 mediated diseases.

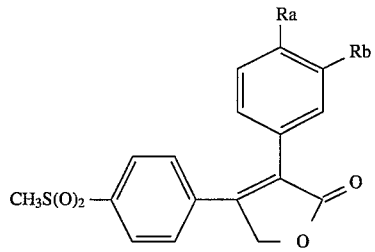

DETAILED DESCRIPTION OF THE INVENTION

The invention encompasses a process for making compounds of Formula I useful in the treatment of inflammation and other cyclooxygenase-2 mediated diseases

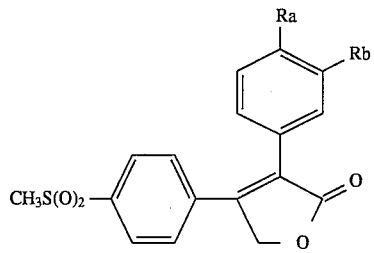

Ra and Rb are each independently selected from the group consisting of
(1) hydrogen, and
(2) halo, wherein halo is defined to include fluoro, bromo and chloro;

the process comprising:
(a) reacting a compound of Formula A1

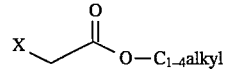

wherein X is chloride or bromo, in a non-reactive solvent and in the presence of a suitable base, with a compound of Formula A2

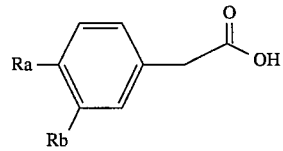

to yield a compound of Formula A3

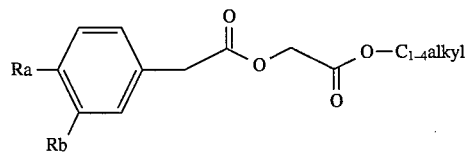

For purposes of this specification non-reactive solvents include halocarbon solvents such solvents as mono or di-halo $C_{1-4}$ alkyl including dichloromethane; etheral solvents such as diethyl ether di-n-butyl and diisopropyl ethers, cyclic ethers such as tetrahydropyran, and tetrahydrofuran; aromatic solvents such as benzene, toluene and xylene; and $C_{6-10}$ linear, branched or cyclic hydrocarbon solvent including hexane. For this step, the non-reactive solvents are preferably acetonitrile or tetrahydrofuran. Suitable bases include but are not limited to pyrrole, pyridine, pyrrolidine, imidazole and lutidine, di $C_{1-3}$ alkylamine such as diisopropylamine and tri $C_{1-3}$ alkylamine such as triethylamine and diisopropyl ethylamine, metal amides, wherein metal is defined as sodium, potassium or lithium, including di-$C_{1-4}$ alkyl amides such as lithium diisopropylamide; $C_{1-4}$ alkyl metals such as n-butyllithium; metal $C_{1-4}$ alkoxides, such as potassium t-butoxide; metal hydrides such as sodium or potassium hydride; and metal carbonates sodium and potassium carbonates. For this step, the suitable bases are preferably triethylamine or diisopropyl ethylamine.

The molar ratio of compound of Formula A1 to compound of Formula A2 may typically be varied from 1: 1.5 to 1.5: 1; preferably 1:1 to 1:1.2. Excess Formula A2 may be used. Similarly, the molar ratio of compound of Formula A1 to base may typically be varied from 1:1.5 to 1.5:1. Preferably the the molar ratio of Formula A1 to base is 1:1 to 1:1.5. The reaction step may conveniently be conducted at a temperature range of 0° to 50° C.; preferably 10° to 25° C. and is allowed to proceed until substantially complete in from 2 to 18 hours; typically 5 to 10 hours.

(b) reacting a compound of Formula A3 in a polar organic solvent, in the presence of a strong base to yield a compound of Formula B1

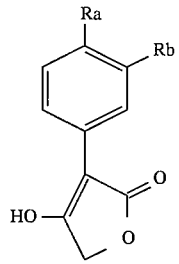

For purposes of this specification the polar organic solvent is defined to include, but is not limited to, N,N-dimethylformamide, tert-butyl alcohol, tetrahydrofuran and dimethylsulfoxide. N,N-dimethylformamide or tert-butyl alcohol are preferred. Similarly, the strong base is defined to include, but is not limited to metal amides, wherein metal is defined as sodium, potassium or lithium, including di-$C_{1-4}$ alkyl amides such as lithium diisopropylamide; metal $C_{1-4}$ alkoxides, such as potassium t-butoxide and metal hydrides such as sodium or potassium hydride. Tert-butoxide (such as potassium tert-butoxide) or 1,8-diazabicyclo[5.4.0] undec-7-ene are preferred.

Typically, molar ratio of compound of Formula A3 to strong base is preferably approximately 1:1 but may vary in either direction by 10%. The reaction step may be conducted at a temperature range of 25° to 80° C.; preferably 70° C., and is allowed to proceed until substantially complete in from 30 minutes to 5 hours; typically 45 minutes to 1 hour.

(c) reacting a compound of Formula B1 in a non-reactive solvent (as defined above), with an activating agent to yield a compound of Formula C1

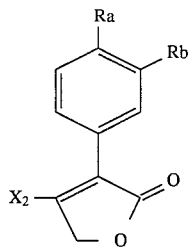

wherein X2 is a good leaving group;

For purposes of this specification the activating agent is defined to include, but is not limited to $PBr_3$; $PCl_5$; $POCl_3$; $(PhO)_2P(O)Cl$; $MeSO_2Cl$; 4-$MePhSO_2Cl$ in the presence of a tri-$C_{1-4}$alkylamine, such as triethylamine; and $(CF_3SO_2)_2O$; $(FSO_2)_2O$ in the presence of a tri$C_{1-4}$alkylamine, such as triethylamine. Accordingly, $X_2$ is defined to include, but is not limited to fluorosulfonate, mesylate, tosylate, Br, Cl, $OP(O)(PhO)_2$ and $OSO_2CF_3$. That is, the activating agent is selected to incorporate one of the desired leaving groups into the compound of Formula C1. In this step the non-reactive solvent is preferably dichloromethane, acetonitrile or tetrahydrofuran.

Typically the molar ratio of compound of Formula B1 to compound of activating agent may conviently be varied from approximately 1.2:1 to 1:1.2, but additional activating agent may be used. Similarly, the molar ratio of compound of Formula B1 to base may conviently be varied from 1:1 to 1:1.5; preferably 1:1.2. The reaction step may be conducted at a temperature range of −10° to 50° C.; preferably 0° to 25° C. and is allowed to proceed until substantially complete in from 5 minutes to 5 hours; typically 30 minutes to 2 hours.

(d) coupling a compound of Formula C1 with a compound of Formula D2

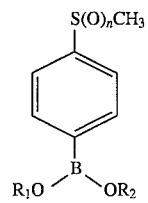

wherein n is 0, 1 or 2; $R_1$ and $R_2$ are each independently selected from H or $C_{1-4}$ alkyl or $R_1$ and R2 are joined, such that together with the atoms to which they are attached there is formed the compound of the formula

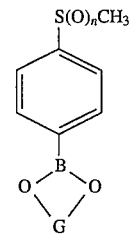

wherein G is a saturated or unsaturated monocyclic carbon ring of 5, 6 or 7 atoms, the coupling step being conducted in a coupling solvent in the presence of a coupling base and a transition metal catalyst to yield a compound of Formula D3

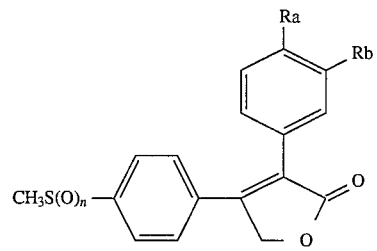

and where n is 0 or 1, oxidizing the compound of Formula D3 to a compound of Formula I.

For purposes of this specification coupling bases include but are not limited to metal hydroxides including barium, potassium, sodium, or lithium, thallium hydroxides; metal $C_{1-4}$ alkoxide such as sodium, potassium or lithium t-butoxide; and metal carbonate such as potassium or sodium carbonates. The coupling solvent is defined to include di-$C_{1-3}$alkyl formamide such as dimethyl formamide, di-C $_{1-3}$alkyl sulfoxide such as dimethylsulfoxide, N-methylpyrrolidinone, N-ethylpyrrolidinone and sulfolane as well as halocarbon solvents such solvents as mono or di-halo $C_{1-4}$ alkyl including dichloromethane; etheral solvents such as diethyl ether di-n-butyl and diisopropyl ethers, cyclic ethers such as tetrahydropyran, and tetrahydrofuran; aromatic solvents such as benzene, toluene and xylene; and $C_{6-10}$ linear, branched or cyclic hydrocarbon solvent including hexane.

For purposes of this specification transition metal catalyst is defined to include Pd° catalysts including Pd (dba)$_2$, Pd$_2$ (dba)$_3$, Pd$_2$ (dba)$_3$·CHCl$_3$ wherein dba is defined as dibenzyledineacetone and Pd(triphenylphosphorous)$_4$. As appreciated by those of skill in the art, other standard coordinating ligands may also be used. Pd$^{II}$ catalysts may also be employed including Pd(OAc)$_2$ and PdCl$_2$. Nickel catalysts may also be used.

Typically the molar ratio of compound of Formula C1 to compound of D2 may conviently be varied from 1.5:1 to 1:1.5; prefereably 1:1.2. Excess D2 may be used. Similarly, the ratio of compound of Formula C1 to transition metal catalyst is typically 1:0.02 to 1:0.10; preferably about 1:0.05. The reaction step a may be conducted at a temperature range of 30° to 80° C.; preferably 57° to 62° C., and is allowed to proceed until substantially complete in from 2 to 20 hours; typically 4 to 5 hours.

Illustrative of the compound of formula D$_2$ when R$_1$ and R$_2$ are joined is:

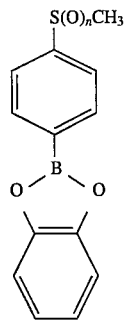

The oxidation may be accomplished by a number of means available in the art. See, for example *Can. J. Chem.* 59, 720 (1981), *Can. J. Chem.* 60, 618 (1982), *J. Chem. Soc.* (C) 1969, 233, *J. Org. Chem.*, 28, 1140 (1963), *Org. Prep. Proceed. Int*, 13, 137 (1981), *J. Org. Chem.*, 50, 1544, (1985), *Chem. Ber.*, 119, 269, (1986), and *Synthesis*, 1015, 1987. We have found oxidation with oxone in a two phase solvent to be surprisingly superior in that undesired side-reaction oxidations are minimized. In this step 2 to 5 equivalents or more of oxidant per mole of compound of Formula D3 may be used. The two phase solvents include but are not limited to methanol in water, methylene chloride in water, and toluene in water. In addition, when a two phase solvent system is used, a phase transfer catalyst such as a tetra $C_{1-4}$alkylammonium halide or other salt, (such tetra-n-butylammonium salts, Aliquat 336, Triton B) or polyethylglycol reagents (such as TWEEN 40) may be added to the reaction mix (0 to 5% of total volume). The reaction step a may be conviently be conducted at a temperature range of 10° to 35° C.; preferably 25° C., and is allowed to proceed until substantially complete in from 5 to 15 hours; typically 4 to 5 hours.

Preferably, Ra and Rb are each independently hydrogen or fluoro. Other choices are disclosed in Table 1.

Most preferable compounds of Formula I are 3-(3,4-Difluorophenyl)-4-(4-(methylsulfonyl)phenyl)-2-(5H)-furanone, and 3-phenyl-4-(4-(methylsulfonyl)phenyl)-2-(5H)-furanone.

The reagent compound of Formula D2 is prepared by reacting a compound of Formula E1

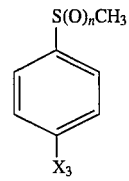

wherein X$_3$ is chloro or bromo, in a non-reactive solvent (as defined above) with $C_{1-4}$alkyllithium to yield a compound of Formula D2, as shown in the following scheme:

SCHEME I

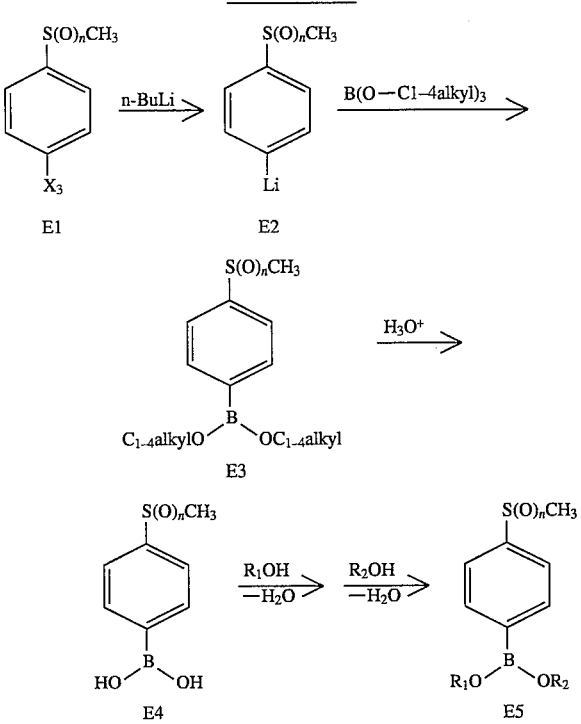

In overview, E1 undergoes metallation with n-butyl lithium; is then boronated, for example with B(O-i-propyl)$_3$; and is then acidified to form E4. Further reaction with R$_1$OH and R$_2$OH wherein R$_1$ and R$_2$ are defined as above provides the intermediate boronic esters.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

By virtue of its high cyclooxygenase-2 (COX-2) activity and/or its selectivity for cyclooxygenase-2 over cyclooxygenase-1 (COX-1 ) as defined above, compounds of formula I will prove useful as an alternative to conventional nonsteroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 $\mu$M. By way of comparison, Ibuprofen has an IC50 for COX-2 of 1 $\mu$M, and Indomethacin has an IC50 for COX-2 of approximately 100 nM.

For the treatment of any of these cyclooxygenase mediated diseases, compounds of formula I may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, s saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 rag, 50 mg, 100 mg, 200 mg, 300 mg, 400 mg, 500 mg, 600 mg, 800 rag, or 1000 mg.

Assays for Determining Biological Activity
Representative Rat Paw Edema Assay- Protocol Male Sprague-Dawley rats (150–200g) were fasted overnight and were given po either vehicle (5% tween 80 or 1% methocel) or a test compound at 9–10 am. One hr later, a line was drawn using a permanent marker at the level above the ankle in one hind paw to define the area of the paw to be monitored. The paw volume ($V_{Oh}$) was measured using a plethysmometer (Ugo-Basile, Italy) based on the principle of water displacement. The animals were then injected subplantarly with 50 ul of a 1% carrageenan solution in saline (FMC Corp, Maine) into the paw using an insulin syringe with a 25-gauge needle (i.e. 500 ug carrageenan per paw). Three hr later, the paw volume ($V_{3h}$) was measured and the increases in paw volume ($V_{3h}-V_{Oh}$) were calculated. The animals were euthanized by $CO_2$ aphyxiation and the absence or presence of stomach lesions scored. Stomach scores were expressed as the sum of total lesions in mm. Paw edema data were compared with the vehicle-control group and percent inhibition calculated taking the values in the control group as 100%. Since a maximum of 60–70% inhibition (paw edema) was obtained with standard NSAIDs, $ED_{30}$ values were used for comparison. All treatment groups were coded to eliminate observer bias. With this protocol, the $ED_{30}$ for Indomethacin is 1.0 mg/kg. Representative results are shown in Table I.

TABLE I

| | STRUCTURE |
|---|---|
| 0.35 | (structure with $SO_2Me$, O, F, F) |
| 0.38 | (structure with $SO_2Me$, O) |
| ~1.00 | (structure with $SO_2Me$, O, Br, F) |
| 0.22 0.23 | (structure with $SO_2Me$, O, Cl, Cl) |
| 0.43 | (structure with $SO_2Me$, O, Cl, F) |

TABLE I-continued

STRUCTURE

| | |
|---|---|
| 0.33 | 3-(3-fluorophenyl)-4-(4-methylsulfonylphenyl) furanone structure |
| 0.46 | 3-(4-bromo-3-methylphenyl)-4-(4-methylsulfonylphenyl) furanone structure |
| 0.76 | 3-(3,4-dibromophenyl)-4-(4-methylsulfonylphenyl) furanone structure |
| 0.48 | 3-(3,4-difluorophenyl)-4-(4-sulfamoylphenyl) furanone structure |
| 0.46 | 3-(3,4-dichlorophenyl)-4-(4-sulfamoylphenyl) furanone structure |
| 0.26 | 3-(3-chloro-4-fluorophenyl)-4-(4-methylsulfonylphenyl) furanone structure |
| 0.55 | 3-(4-bromo-3-fluorophenyl)-4-(4-methylsulfonylphenyl) furanone structure |

The invention will now be illustrated by the following non-limiting examples in which, unless stated otherwise:

(i) all operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) or High Pressure Liquid Chromatography (HPLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Ac=acetyl
Bn=benzyl
DBU=1,8-diazabicyclo[5.4.0]undec-7-ene
DMF=N, N-dimethylformamide
$Et_3N$=triethylamine
LDA=lithium diisopropylamide
Ms=methanesulfonyl=mesyl=$SO_2Me$
MsO=methanesulfonate=mesylate
NSAID=non-steroidal anti-inflammatory drug
OXONE®=$2KHSO_5 \cdot KHSO_4 \cdot K_2SO_4$
Ph=phenyl
r.t.=room temperature
rac.=racemic
THF=tetrahydrofuran TLC=thin layer chromatography
Pd(triphenyl-P)$_4$ =Pd(triphenylphosphorous)$_4$ Alkyl Group Abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

EXAMPLE 1

3-phenyl-4-(4-methylsulfonyl)phenyl-2(5H)-furanone

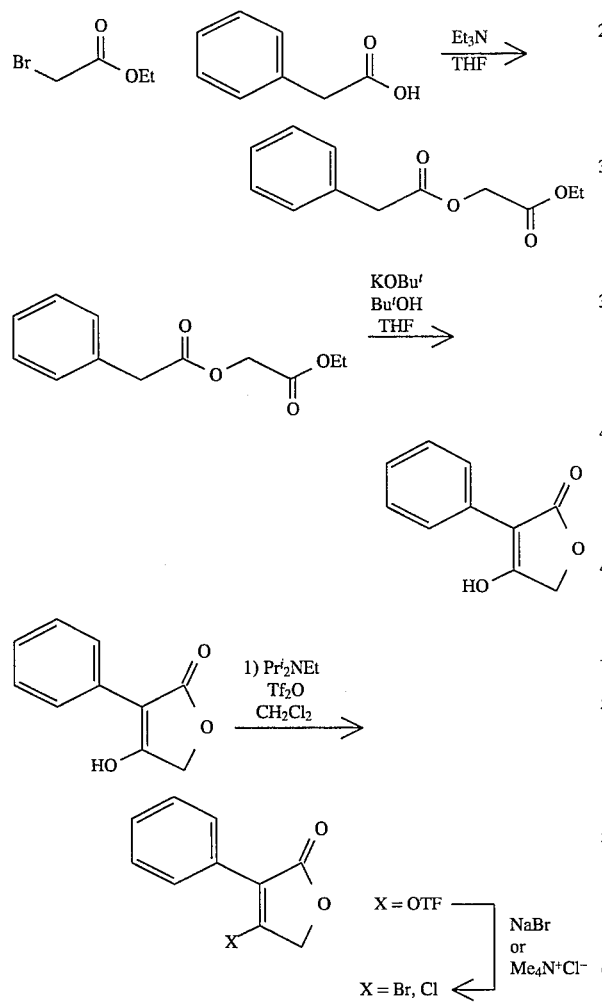

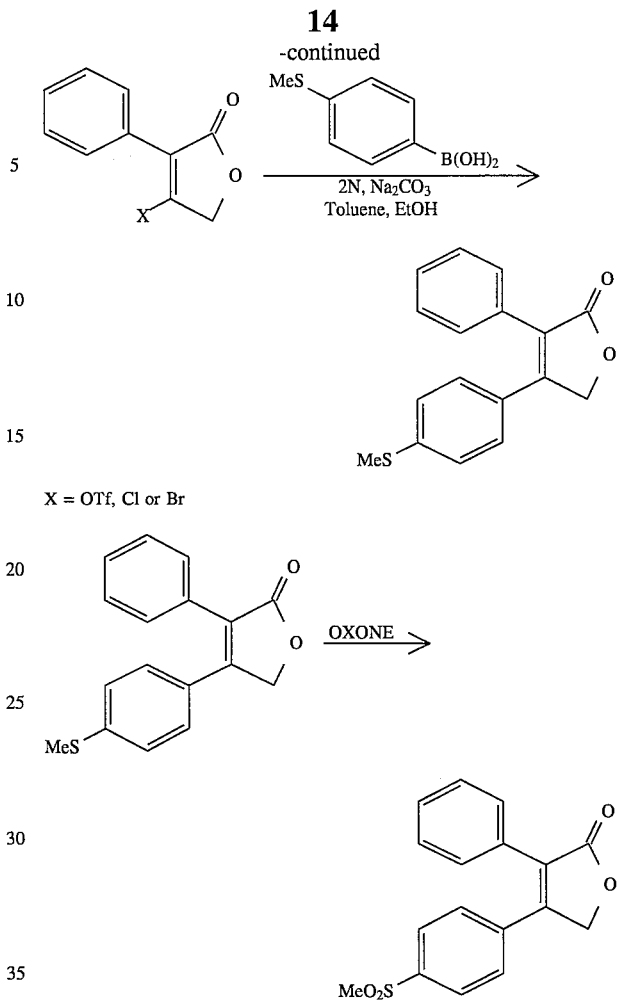

Step A Preparation of the ester

To a stirred solution of phenylacetic acid (100 g, 1 equiv) and ethyl bromoacetate (77.4 mL, 0.95 equiv.) in THF (1000 mL) was added triethylamine (107.5 mL, 1.05 equiv.), and the resulting mixture was heated to 60° C. for 1 h (nitrogen atmosphere). The mixture was cooled to 25° C. and was then poured into a stirred mixture of ethyl acetate (1000 mL) and water (1000 mL). The layers were separated, the aq. layer was extracted with ethyl acetate (600 mL) and the combined organic extracts were washed with sat. sodium bicarbonate solution (500 mL) and with brine (300 mL). The solvent was removed under reduced pressure to give the ester (145 g, 94%). 1H nmr, 300 MHz, CDCl3), 1.25 (3H, t, J=7 Hz), 3.75 (2H, s), 4.20 (2H, q, J=7 Hz), 4.60 (2H, s), 7.2–7.4 (5H, m).

Step B Preparation of the tetronic acid

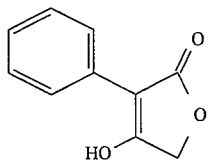

To a stirred solution of potassium tert-butoxide (10 g, 1 equiv.) in tert-butanol (80 mL) at 25° C. (nitrogen atmosphere) was added the ester (10g, 1 equiv.). The mixture was heated to 70° C. for 60 min and then water (100 mL) and methyl tert-butyl ether (100 mL) were added. The layers were separated and the organic layer extracted with H2O (50 mL). The combined aqueous extracts were washed with methyl tert-butyl ether (50 mL) and were then acidified to pH 4 with 2N aqueous HCl. The white precipitate thus obtained was filtered and dried by suction to give the tetronic acid (5.65 g, 72%). $^1$H nmr (300 MHz, DMSO), 4.75 (s, 2H), 7.22 (1H, t, J=8 Hz), 7.45 (2h, t, J=8 Hz), 7.9 (2H, d, J=8 Hz).

Step C Preparation of triflate

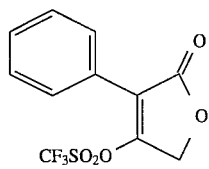

To a cold (0° C.), stirred solution of the tetronic acid (680 mg, 1 equiv.) in CH$_2$Cl$_2$ (10 mL) was added N,N-diisopropylethylamine (0.74 mL, 1.1 equiv.) followed by trifluoromethanesulfonyl anhydride (0.65 mL, 1 equiv) (nitrogen atmosphere). The solution was stirred for 10 min at 0° C. and was then poured into a stirred mixture of H$_2$O (10 mL) and ethyl acetate (20 mL). The layers wetre separated and the organic layer was washed with 1N HCl (10 mL) and then with water (10 mL). The solvent was removed to give the triflate as a yellow oil (which solidified upon storage at −10° C.). $^1$H nmr (300 MHz, CDCl$_3$)5.08 (2H, s), 7.4–7.5 (3H, m), 7.7–7.8 (2H, m).

Step D Preparation of the bromide

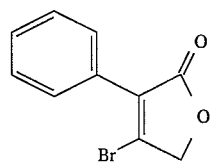

A mixture of the triflate (15.3 g, 1 equiv) and lithium bromide (25 g, 5 equiv) in acetone (100 mL) was heated at 50 ° C. for 30 min (nitrogen atmosphere). The mixture was cooled to 25° C. and was then partitioned between ethyl acetate (200 mL) and H2O (100 mL). The aqueous layer was extracted with ethyl acetate (50 mL) and the combined organic extracts were washed with brine (50 mL) and were then concentrated to give the bromide (11.28 g, 90%). 1H nmr (300 MHz, CDCl3), 4.85 (2H, s), 7.4–7.5 (3H, m), 7.7–7.8 (2H, m).

Step E Preparation of 4-methylthio-phenylboric acid

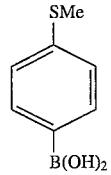

To a cold (−75° to −78° C.), stirred solution of 4-bromothioanisole (20 g, 1 equiv.) and triisopropyl borate (33 mL, 1.45 equiv.) in dry THF (350 mL) was slowly added a solution of n-butyllithium (1.5 M in hexanes) over 3 h (nitrogen atmosphere). The resulting mixture was then stirred at −78° C. for 30 min and then was allowed to warm to 25° C. over 1 h. Aqueous sulfuric acid (2 M, 200 mL) was added slowly (internal temperature rose to 30° C. during addition) and the mixture was stirred at 25° C. for 2 h. The layers were separated and the aqueous layer was extracted with ethyl acetate (2×100 mL). The combined organic extracts were then concentrated to approx. 30 mL and to the resulting slurry was added water (100 mL). The miture was stirred for 10 h, and the solid was filtered and was the washed with toluene and dried by suction, to give the boronic acid (15.9 g, 95%). 1H nmr (300 MHz, DMSO), 2.5 (3H, s), 7.18 (2H, d, J=8 Hz), 7.70 (2H, d, J=8 Hz), 7.95 (2H, br s).

Step F Preparation of 3-phenyl-4-(methylthio)phenyl-2-(5H)-furanone via the triflate.

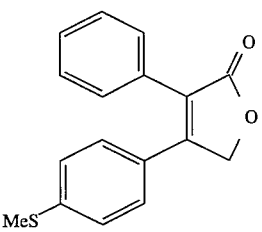

To a solution of the triflate (465 mg, 1 equiv.), Pd(tri-phenyl-P)$_4$ (87 mg, 0.05 equiv.) in degassed toluene (3 mL) (nitrogen atmosphere) was added aq sodium carbonate (2.1 equiv, 1.6 mL of a 2M solution) and the stirred mixture was heated to 60° C. A solution of the boronic acid (304 mg, 1.2 equiv.) in ethanol (1.6 mL) was added in one batch and the resulting mixture was heated at 60° C. for 2 h. The mixture was cooled to 25° C. and was then partitioned between ethyl acetate (10 mL) and water (5 mL). The organic layer was then concentrated to give a crude oil which was chromatographed on silica gel (30% EtOAc-70% hexanes) to give the furanone (317 mg, 70%). 1H nmr (300 MHz, 5.17 (2H, s), 7.16 (2H, d, J=8 Hz), 7.23 (2H, d, J=8 Hz), 7.35–7.45 (5 H, m).

Preparation of 3-phenyl-4-(methylthio)phenyl-2-(5H)-furanone via the bromide.

To a solution of the bromide (234 rag, 1 equiv.), Pd(PPh3)4 (55 mg, 0.05 equiv.) in degassed toluene (2 mL) (nitrogen atmosphere) was added aq sodium carbonate (2.1 equiv, 1.0 mL of a 2M solution) and water (1 mL) and the stirred mixture was heated to 60° C. A solution of the boronic acid (198 mg, 1.2 equiv.) in ethanol (0.75 mL) was added in one batch and the resulting mixture was heated at 60° C. for 9 h. The mixture was cooled to 25° C. and was then partitioned between ethyl acetate (10 mL) and water (5 mL). The organic layer was then concentrated to give a crude oil which was chromatographed on silica gel (30% EtOAc-70% hexanes) to give the furanone (265 mg, 90%).

Step G. Preparation of 3-phenyl-4-(4-methylsulfonyl)phenyl-2(5H)-furanone

The sulfide (1g) and tetrabutylammonium bromide (0.034g) were dissolved in methylene chloride(15ml) at 25° C. Water (25ml) and oxone (2.7g) were added and the temperature was maintained at 25–30° C. for 24h. The layers were separated and the organic layer was washed with water (20ml). The organic was concentrated to dryness in vacuo to afford the desired sulphone (0.9g).

EXAMPLE 2

3-(3,4-Difluorophenyl)-4-(4-(methylsulfonyl)phenyl)-2-(5H)-furanone

The title compound is prepared as described in Example 1, by substitution of the 3,4-di-fluoro ester:

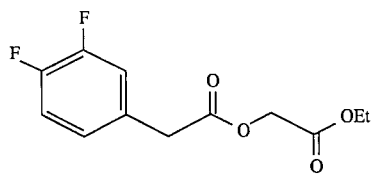

for that described in Example 1, Step A.

What is claimed:

1. A process for making compounds of Formula I

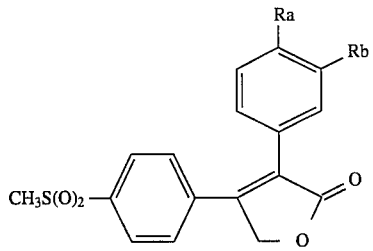

Ra and Rb are each independently selected from the group consisting of
(1) hydrogen, and
(2) halo;

the process comprising:
coupling a compound of Formula C1 where $X_2$ is a leaving group

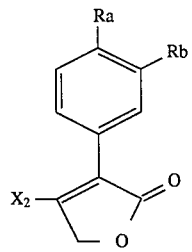

with a compound of Formula D2

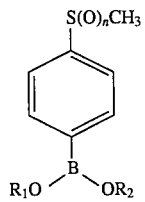

wherein n is 0, 1 or 2;
R1 and R2 are each independently selected from H or $C_{1-4}$alkyl or $R_1$ and $R_2$ are joined, such that together with the atoms to which they are attached there is formed the compound of the formula

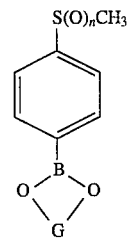

whererin G is a mono-cyclic saturated or unsaturated carbon ring of 5, or 7 atoms, the coupling step being conducted in a coupling solvent in the presence of a coupling base and a transition metal catalyst to yield a compound of Formula D3

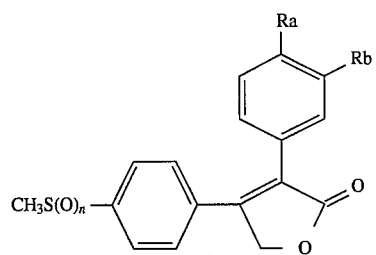

and where n is 0 or 1, oxidizing the compound of Formula D3 to a compound of Formula I.

2. A process according to claim 1 wherein the coupling solvent is toluene or diethoxymethane; the coupling base is potassium carbonate or sodium carbonate; and the transition metal catalyst is Pd(triphenyl-P)4.

3. A process of claim 2 wherein
wherein n is 0;
$R_1$ and $R_2$ are each independently selected from H or $C_{1-4}$alkyl, and the coupling is conducted at 55° to 62° C.

4. A process according to claim 1 comprising the steps of reacting a compound of Formula B1

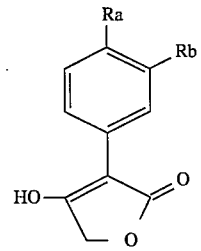

in a non-reactive solvent, with an activating agent to yield a compound of Formula C1

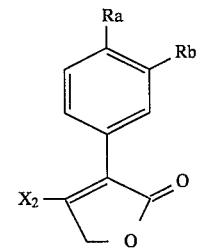

wherein $X_2$ is a good leaving group; and
coupling a compound of Formula C1 with a compound of Formula D2

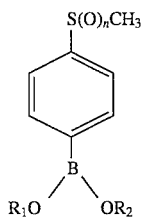

wherein n is 0, 1 or 2;

$R_1$ and $R_2$ are each independently selected from H or $C_{1-4}$alkyl or $R_1$ and $R_2$ are joined, such that together with the atoms to which they are attached there is formed the compound of the formula

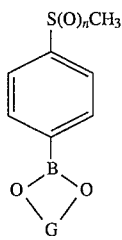

wherein G is a mono-cyclic saturated or unsaturated carbon ring of 5, 6 or 7 atoms, the coupling step being conducted in a coupling solvent in the presence of a coupling base and a transition metal catalyst to yield a compound of Formula D3

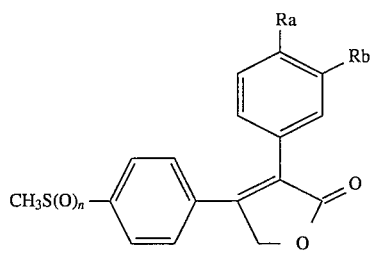

and where n is 0 or 1, oxidizing the compound of Formula D3 to a compound of Formula I.

5. A process of claim 4 wherein the coupling solvent is toluene or diethoxymethane; the coupling base is potassium carbonate or sodium carbonate; the transition metal catalyst is Pd(triphenyl-P)$_4$; the non-reactive solvent is acetonitrile or tetrahydrofuran, and the activating agent is PBr$_3$ or PCl$_5$ or POCl$_3$ or (PhO)$_2$P(O)Cl or MeSO$_2$Cl or 4-MePhSO$_2$Cl in the presence of a tri-$C_{1-4}$alkylamine or (CF$_3$SO$_2$)$_2$O or (FSO$_2$)O in the presence of a triC$_{1-4}$alkylamine.

6. A process of claim 4 wherein n is 0;

$X_2$ is chloro or bromo;

$R_1$ and $R_2$ are each independently selected from H or $C_{1-4}$alkyl, the coupling is conducted at 55° to 62° C., and the reacting of compound B1 with activating agent is conducted at 0° to 25° C.

7. A process according to claim 4 comprising the steps of reacting a compound of Formula A3

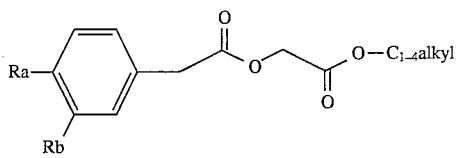

in a polar organic solvent, in the presence of a strong base to yield a compound of Formula B1

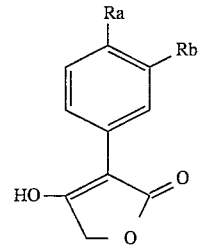

reacting a compound of Formula B1 in a nonreactive solvent, with an activating agent to yield a compound of Formula C1

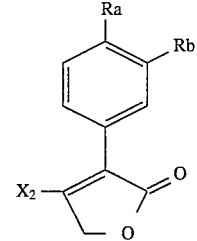

wherein $X_2$ is a good leaving group; and coupling a compound of Formula C1 with a compound of Formula D2

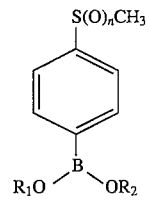

wherein n is 0, 1 or 2;

$R_1$ and $R_2$ are each independently selected from H or $C_{1-4}$alkyl or $R_1$ and $R_2$ are joined, such that together with the atoms to which they are attached there is formed the compound of the formula

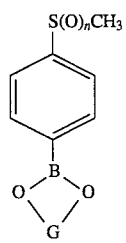

wherein G is a mono-cyclic saturated or unsaturated carbon ring of 5, 6 or 7 atoms, the coupling step being conducted in a coupling solvent in the presence of a coupling base and a transition metal catalyst to yield a compound of Formula D3

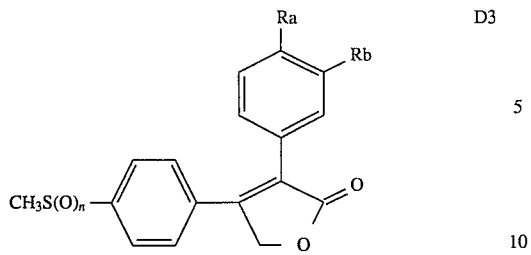

and where n is 0 or 1, oxidizing the compound of Formula D3 to a compound of Formula I.

8. A process of claim 7 wherein the coupling solvent is toluene or diethoxymethane; the coupling base is potassium carbonate or sodium carbonate; the transition metal catalyst is Pd(triphenyl-P)$_4$; the oxidation is conducted with oxone; the non-reactive solvent is acetonitrile or tetrahydrofuran; the activating agent is PBr$_3$ or PCl$_5$ or POCl$_3$ or (PhO)$_2$P(O)Cl or MeSO$_2$Cl or 4-MePhSO$_2$Cl in the presence of a tri-C$_{1-4}$alkylamine or (CF$_3$SO$_2$)$_2$O or (FSO$_2$)O in the presence of a tri-C$_{1-4}$alkylamine; the polar organic solvent is N,N-dimethylformamide or tert-butyl alcohol; and the strong base is a sodium or potassium C$_{1-4}$alkyloxide.

9. A process of claim 8 wherein n is 0;

X$_2$ is bromo or chloro;

R$_1$ and R$_2$ are each independently selected from H or C$_{1-4}$alkyl, and the coupling is conducted at 55° to 62° C., the reacting of compound B1 with activating agent is conducted at 0° to 25° C., and the reacting of compound A3 with strong base is conducted at 68° to 72° C.

10. A process according to claim 7 comprising the steps of reacting a compound of Formula A1

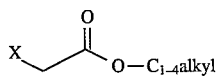

wherein X is chloride or bromo, in a non-reactive solvent and in the presence of a suitable base, with a compound of Formula A2

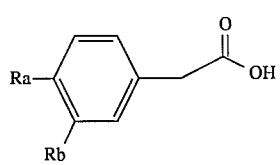

to yield a compound of Formula A3

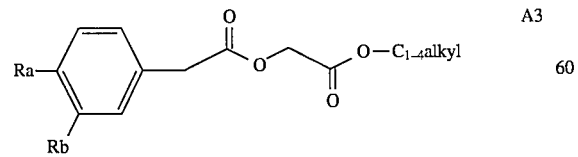

reacting a compound of Formula A3 in a polar organic solvent, in the presence of a strong base to yield a compound of Formula B1

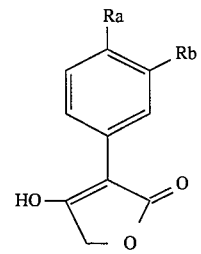

reacting a compound of Formula A3 in a polar organic solvent, in the presence of a strong base to yield a compound of Formula B1

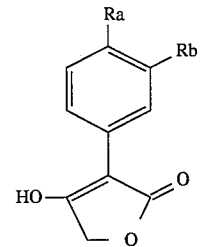

reacting a compound of Formula B1 in a non-reactive solvent, with an activating agent to yield a compound of Formula C1

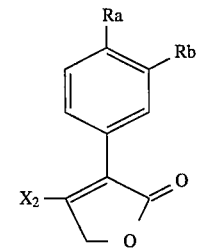

wherein X$_2$ is a good leaving group; and coupling a compound of Formula C1 with a compound of Formula D2

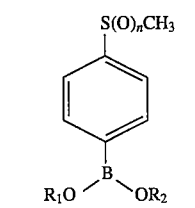

wherein n is 0, 1 or 2;

R$_1$ and R$_2$ are each independently selected from H or C$_{1-4}$alkyl or R$_1$ and R$_2$ are joined, such that together with the atoms to which they are attached there is formed the compound of the formula

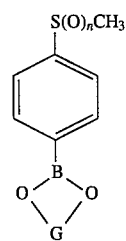

wherein G is a mono-cyclic saturated or unsaturated carbon ring of 5, 6 or 7 atoms, the coupling step being conducted in a coupling solvent in the presence of a coupling base and a transition metal catalyst to yield a compound of Formula D3

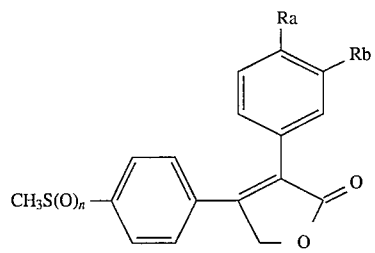

and where n is 0 or 1, oxidizing the compound of Formula D3 to a compound of Formula I.

11. A process of claim 10 wherein the coupling solvent is toluene or diethoxymethane; the coupling base is potassium carbonate or sodium carbonate; the transition metal catalyst is Pd(triphenyl-P)$_4$; the non-reactive solvent is acetonitrile or tetrahydrofuran; the activating agent is PBr$_3$ or PCl$_5$ or POCl$_3$ or (PhO)$_2$P(O)Cl or MeSO$_2$Cl or 4-MePhSO$_2$Cl in the presence of a tri-C$_{1-4}$alkylamine or (CF$_3$SO$_2$)$_2$O or (FSO$_2$)O in the presence of a tri-C$_{1-4}$alkylamine; the polar organic solvent is N,N-dimethylformamide or tert-butyl alcohol; and the strong base is a sodium or potassium C$_{1-4}$alkyloxide.

12. A process of claim 11 wherein n is 0;

X$_2$ is bromo or chloro;

R$_1$ and R$_2$ are each independently selected from H or C$_{1-4}$alkyl, and the coupling is conducted at 55° to 62° C., the reacting of compound B1 with activating agent is conducted at 0° to 25° C., the reacting of compound A3 with strong base is conducted at 68° to 72° C., and the reacting of compound A1 with A2 is conducted at 0° to 25° C.

13. A compound selected from the group consisting of

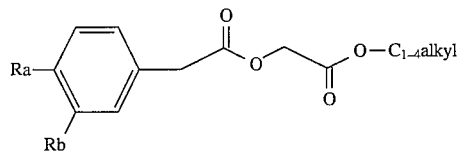

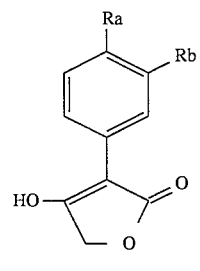

or

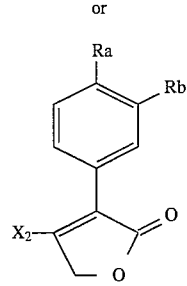

wherein

X$_2$ is bromo or chloro; and

Ra and Rb are each independently selected from the group consisting of
(1) hydrogen, and
(2) fluoro, bromo or chloro.

14. A compound according to claim 12 wherein Ra and Rb are both hydrogen or are both fluoro.

* * * * *